March 24, 1964 R. S. MOORE Plant Pat. 2,382
ROSE PLANT
Filed Jan. 12, 1962
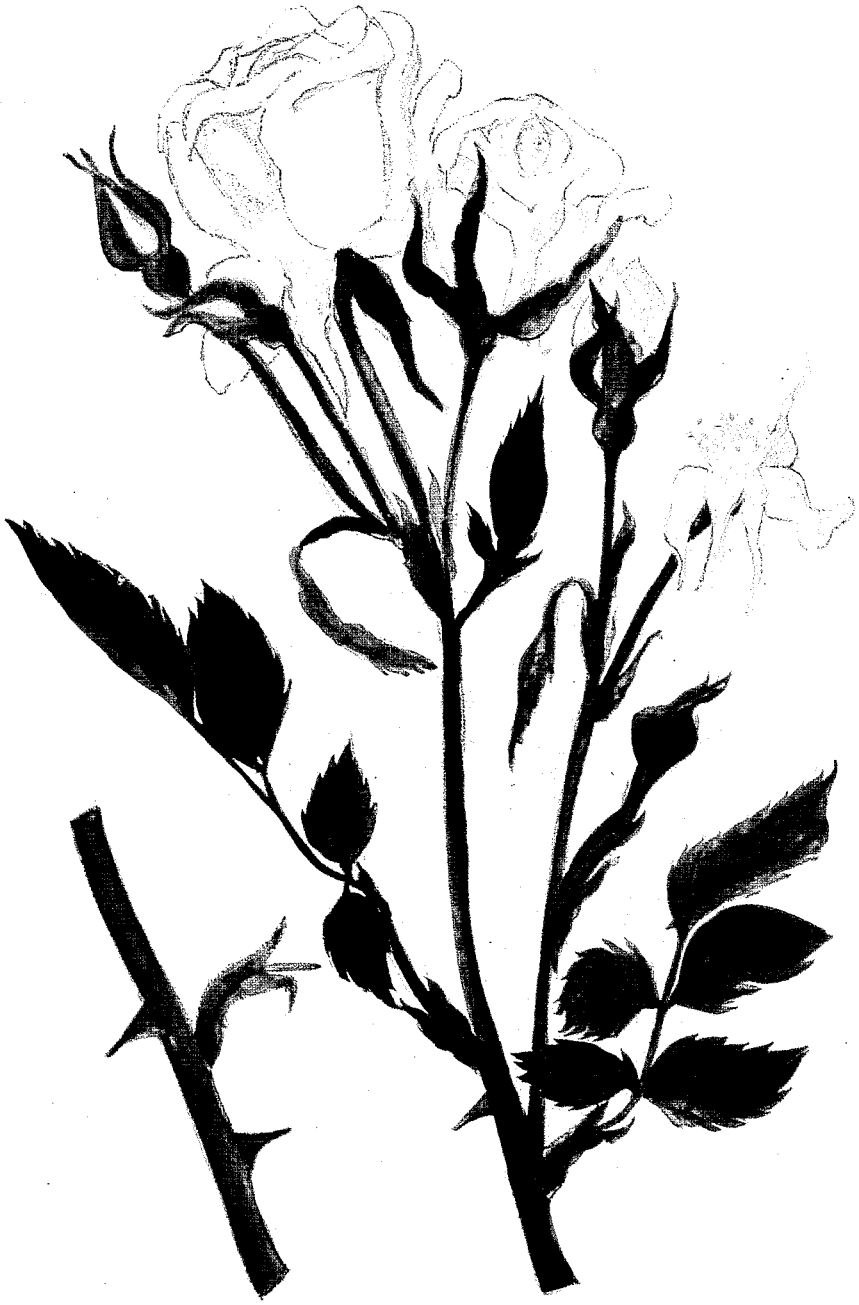
WITNESS
Jeanette Nunn Copley
INVENTOR
RALPH S. MOORE
ATTORNEYS United States Patent Office Plant Pat. 2,382
Patented Mar. 24, 1964

2,382
ROSE PLANT

Ralph S. Moore, 2519 E. Mineral King, Visalia, Calif.

Filed Jan. 12, 1962, Ser. No. 165,973
1 Claim. (Cl. Plt.—24)

This invention relates to a new and distinct variety of dwarf, bush-type floridbunda rose plant.

This plant is characterized as to novelty by its sprawling and full growth habit.

This floridbunda rose resembles Moonsprite (U.S. Plant Patent 1,450) in color and shape and Pinkie (U.S. Plant Patent 712) in growth habit.

The new variety is ideal for edging or border use be-because the lower branches and foliage fill down to the ground. The plant habit also makes thihs new variety well suited for growing in containers such as redwood tubs for patio decoration. The flowers are very abundant, and it is not unusual to find from 10–20 flowers and buds on one stem, with from 40 to 50 ivory-colored petals on each bloom.

This variety of floribunda rose plant was originated by me, in my nursery located at Visalia, California, and under conditions of careful control and observation, as a cross between Golden Glow (U.S. Plant Patent 263) as the seed parent and Zee (not patented) as the pollen parent. Subsequent to origination of the variety, I successfully asexually reproduced it in my nursery, located as aforesaid, by budding as well as cuttings, the reproductions having run true in all respects.

The drawing illustrates the variety including foliage, buds and flowers.

Referring now specifically to the new and distinct variety of floribunda rose plant, the following is a detailed description thereof in outline; all major color plate identifications being to the British Colour Council Horticultural Colour Chart, except where common terms of color definition are employed.

Type: Dwarf; bush; half hardy; outdoor; seedling; cut flowers; garden decoration.
Class: Floribunda.

*Flowers*

Continuity: Intermittent to continuous.
Fragrance: Slight to moderate.
Flowers borne: From 3–4 to several on each stem (up to 10–20 flowers and buds may appear on one stem); flowers grown in regular, rounded clusters; stems are of normal strength and short to medium length.
Quantity of bloom: Free, outdoors.
Bud:
*Peduncle.* — Medium length; slender; medium strength; medium green.
*Before calyx breaks.*—Size—small to medium. Form—pointed oval, with tiny (short) reddish hairs on the surface of the bud, with foliaceous parts extending beyond the tip of the bud equal to ¼ or more of its length. Color—green.
*As calyx breaks.*—Color—light greenish white.
*As first petal opens.*—Size—medium. Form—pointed, ovoid. Color: outside—near Uranium Green 63/3, becoming Dresden Yellow 64/4 thence shading to near white near petal tips; inside—shading from Dresden Yellow 64/2 at base of petal thence through Uranium Green (between 63/2 and 63/3) into near white in outer ½ of petal. Opening—opens well in all weather.
Bloom:
*Size when fully opened.*—Medium, 2½" to 2¾".
*Pentalage.*—Double, with from 40 to 50 petals arranged regularly.

*Form.*—Flat and full at first; becoming open and cupped; petals remaining at first very loosely rolled outward; becoming later, at maturity, very loose and flat cupped, with the outer petals rolled outward.
Petals: Of medium thickness; inside satiny; outside satiny.
*Shape.*—Outside—broad obovate; intermediate—obovate; inside—obovate or spatulate.
*Color.*—Newly opened flower from plant grown outdoors (September)—Outside petal: outside surface with just a touch of Uranium Green (between 63/2 and 63/3) at base shading to white or near white for rest of petal; inside surface with a touch of Dresden Yellow 64/2 at base shading into Dresden Yellow 64/3 thence lighter into white. Intermediate petal: outside surface similar to inside surface above but with yellow extending farther up petal); inside surface same as outside surface. Inner petal: outside surface Dresden Yellow 64/2 at base, shading into 64/3, thence to near white at petal tip; inside surface same as outside surface. Rose opened for three days outdoors (September)—Outside petal: outside surface Dresden Yellow 64/3 or lighter at base, shading quickly into white; inside surface same as outside surface. Inside petal: outside surface and inside surface same as outside petals.
*General color effect.*—Newly opened flower—ivory (creamy) white. Three days open—white.
*Behavior.*—Persist for a time; buds and opening flowers may be more yellow in cooler weather.
*Flower longevity.*—Three to five days on bush in garden (September). Three to four days as cut roses grown outdoors, kept at living room temperatures (September).
Reproductive organs:
*Stamens.*—Few to medium number; arranged irregularly about pistils.
*Filaments.*—Short to medium; light yellow; most with anthers.
*Anthers.*—Medium size; yellow; open all at once.
*Pollen.*—Of moderate quantity; lemon.
*Pistils.*—Of medium quantity.
*Styles.*—Uneven; short to medium length; loosely separated.
*Stigma.*—Light yellow.
*Ovaries.*—Enclosed in calyx.
*Hips.*—None.
*Sepals.*—Permanent; of moderate length; spear shaped, recurved (usually folded back around stem or neck); green becoming brown.
*Seeds.*—None.

*Plant*

Foliage:
*Leaves.*—Compound of 5 to 7 leaflets; normally abundant; moderately small; thin; leathery.
*Leaflets.*—Shape lanceolate. Apex—Base—round. Margin—serrate.
*Color.*—Mature: upper surface—normal green; under surface—normal green. Young: upper surface—green edged with bronze to red; under surface—normal green overlaid with bronze to red.
*Rachis.*—Light; upper side smooth and grooved; under side sparsely thorny, with from 2–3 small thorns.
*Stipules.*—Of medium length; moderately narrow; with short points turning out at an angle of more than 45°.
*Disease.*—Resistant to mildew as compared with other varieties grown under comparable cultural conditions at Visalia, California.

Growth:

*Habit.*—Dwarf; bushy; sprawling; many branches.

*Growth.*—Moderate.

*Canes.*—Light to medium.

*Main stems.*—Color—green. Thorns—several, of medium length, hooked only slightly downward, with oval base. Prickles—none. Hair—none to few.

*Branches.*—Bright green. Thorns—several, of medium length, hooked only slightly downward, with oval base. Prickles—none. Hairs—none.

*New shoots.*—Bright green overlaid with bronze to red. Thorns—few to several, of medium length, hooked only slightly downward. Prickles—none. Hairs—none.

The following is claimed:

A new and distinct variety of floribunda rose plant, substantially as herein shown and described, of the dwarf-bush-type, outdoor variety characterized by its sprawling and full growth habit which places as many as ten to twenty blooms on a stem and which full growth extends to the ground, and by its medium-sized, satiny petals arranged regularly with newly opened flowers of ivory or creamy white and with flowers open for three days blending into white, said growth habit resembling Pinkie and said color resembling Moonsprite.

No references cited.